(12) United States Patent
Ghorbani

(10) Patent No.: US 8,962,045 B2
(45) Date of Patent: *Feb. 24, 2015

(54) HERBAL/ORGANIC COMPOSITION FOR THE MANAGEMENT OF PAIN

(71) Applicant: Reza Ghorbani, Chevy Chase, MD (US)

(72) Inventor: Reza Ghorbani, Chevy Chase, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/334,975

(22) Filed: Jul. 18, 2014

(65) Prior Publication Data

US 2014/0328954 A1    Nov. 6, 2014

Related U.S. Application Data

(63) Continuation of application No. 13/853,104, filed on Mar. 29, 2013, now Pat. No. 8,852,653.

(51) Int. Cl.
*A01N 65/00* (2009.01)
*A61K 36/9068* (2006.01)
*A61K 31/133* (2006.01)
*A61K 31/385* (2006.01)
*A61K 31/60* (2006.01)
*A61K 36/324* (2006.01)
*A61K 36/53* (2006.01)
*A61K 36/76* (2006.01)
*A61K 36/9066* (2006.01)

(52) U.S. Cl.
CPC .......... *A61K 36/9068* (2013.01); *A61K 31/133* (2013.01); *A61K 31/385* (2013.01); *A61K 31/60* (2013.01); *A61K 36/324* (2013.01); *A61K 36/53* (2013.01); *A61K 36/76* (2013.01); *A61K 36/9066* (2013.01)
USPC .......................................................... 424/725

(58) Field of Classification Search
None
See application file for complete search history.

(56) References Cited

U.S. PATENT DOCUMENTS

| | | |
|---|---|---|
| 6,541,041 B1 | 4/2003 | Konishi |
| 6,949,260 B2 | 9/2005 | Krumhar |
| 7,282,224 B1 | 10/2007 | Roederer |
| 7,744,931 B2 | 6/2010 | Newmark et al. |
| 7,777,073 B2 | 8/2010 | Gupta |
| 2003/0031737 A1 | 2/2003 | Rosenbloom |
| 2007/0243270 A1 | 10/2007 | Evans et al. |
| 2009/0220625 A1 | 9/2009 | Herrmann et al. |
| 2012/0082739 A1 | 4/2012 | Ghorbani |

*Primary Examiner* — Michael Meller
(74) *Attorney, Agent, or Firm* — Lowe Hauptman & Ham, LLP

(57) ABSTRACT

An herbal/organic composition for the treatment and management of pain contains about 0.01 wgt % *Boswellia* extract, about 0.01 wgt % ginger extract, about 0.01 wgt % holy basil extract, about 0.01 wgt % rosemary extract, about 0.01 wgt % turmeric extract, about 0.01 wgt % white willow extract, about 0.01 wgt % alpha lipoic acid and about 10.0 wgt % trolamine salicylate and about 89.93 wgt % of a carrier such as water. The composition is applied to an around an area of pain two or three times a day for seven to 14 days.

5 Claims, No Drawings

HERBAL/ORGANIC COMPOSITION FOR THE MANAGEMENT OF PAIN

CROSS REFERENCE TO RELATED APPLICATION

The present application is a Continuation of U.S. patent application Ser. No. 13/853,104, filed Mar. 29, 2013, the disclosure of which is herein incorporated by reference in its entirety.

FIELD OF THE INVENTION

This invention relates to an herbal/organic composition for the management of pain and methods utilizing such compositions for the treatment and management of pain in human patients.

BACKGROUND FOR THE INVENTION

In an earlier application filed by Applicant, U.S. patent application Ser. No. 13/036,514 filed on Feb. 28, 2011 and claiming the priority of a U.S. Provisional Application No. 61/388,995, filed Oct. 1, 2010, entitled Compositions and Methods for Treatment and Management of Pain, Applicant discloses an improved composition and method for treatment and management of pain in human patients. The present invention represents a further improvement over my earlier patent application.

In my earlier application, I disclosed and claimed an herbal composition for the management of pain comprising turmeric extract, *Boswellia* extract, ginger extract, holy basil extract, rosemary extract, white willow extract and alpha lipoic acid.

In a preferred embodiment of the present invention, the herbal organic composition for the management of pain includes the following turmeric extract, *Boswellia* extract, ginger extract, holy basil extract, rosemary extract, white willow extract and alpha lipoic acid in equal amounts are present in an amount of about 0.01% by wgt. while the trolamine salicylate is present in the amount of 10% by wgt. Further, a pharmaceutical acceptable carrier is selected from the group consisting of water, glycerol stearate, octinoxate, alphotocapherol (vitamin E), diazolidimylurea, Coco Caprylate/Caprate and Sterearyl Stearate.

Accordingly, there remains a need for easy-to-use formulations having analgesic and/or anti-inflammatory properties that can avoid the drawbacks of the prior art analgesic products.

A number of U.S. Patents and Patent Application Publications disclose various herbal remedies for use in treating various ailments including pain. For example, a U.S. Patent Application Publication of Rosenbloom, No. 2003/0031737 discloses a medicinal composition and method of using it. The composition is used to treat the symptoms of the common cold, a sore throat, congestion, laryngitis, mucous membrane inflammation and sialorrhea. The composition includes ingredients obtainable from turmeric extract, ginger root powder, and horseradish root powder and is administered orally to a patient. The composition may further include ingredients obtainable from slippery elm bark powder and green tea as well as pharmaceutically acceptable carriers for oral administration.

A second reference of Konishi is disclosed in a U.S. Pat. No. 6,541,041 for crude drug extracts and methods for making and standardizing same. The extracts contain soluble silicon compounds as an effective component and are obtained by subjecting a crude drug to extraction with water or an aqueous solvent, preferably at an alkaline pH. The crude drug subjected to extraction may be derived from animals, plants, etc. The quality of the crude drug extract can be standardized using the soluble silicon compounds as an index. Those compounds exhibit inhibitory action towards the production of plasma kallikrein.

A third disclosure is contained in a U.S. Pat. No. 6,949,260 of Krumhar for a method for treatment of inflammation and pain in mammals. The composition contains effective amounts of a boswellic acid, a curcuminoid, a gingerol, a capsaicinoid, a bioflavonoid, and a vitamin C source. These compounds are taken from a biotanical source and are blended to form a dose for oral administration. Administration of the dose provides relief from pain and inflammation of connective tissue. The dose may be administered as a tablet, a liquid, or a powder.

An additional disclosure is disclosed in a U.S. Pat. No. 7,282,224 of Roederer for a pain relief composition. The composition comprises an effective amount of a never inhibiting component, including capsaicin, a capsaicinoid or a capsaicin analogue, which numbs or inhibits the nerve endings that signal pain. Those compounds are combined with at least one of the following: an effective amount of inflammation control component which is designed to reduce immediate pain and discourage future pain in the joints and muscles; an effective amount of a cooling component; an effective amount of a heat minimizing or blocking component; an effective amount of a circulation increasing component which effectuates better penetration of the actives to the skin and nerves and an effective amount of soothing and anti-inflammatory complex for the joints and/or muscles comprising Glusosamine sulfate or HCI, *Zingiber officiniale* (Ginger Root) extract, Methyl sulfonylmethane (MSM), *Polygonum cuspidatum* (Mexican Bamboo) extract, *Alo barbadensis* leaf, and *Salix alba* (white will) bark extract.

A U.S. Patent Application Publication No. 2007/0243270 of Evans et al. discloses methods for reducing cellular damage, inhibiting free radical production and scavenging free radicals in mammals. The methods include (a) administering to the mammal an oral dosage form comprising a therapeutically effective amount of a first antioxidant, and (b) administering to the mammal a topical dosage from comprising a therapeutically effective amount of a second antioxidant, wherein at least one of the first antioxidant and the second antioxidant comprises acerola concentrate. Methods of inhibiting free radical production, methods of scavenging free radicals, and kits for reducing cellular damage are also described.

A still further disclosure is disclosed in a U.S. Patent Application Publication No. 2009/0220625 of Herrmann et al. This publication discloses a synergistic mixture of bisabolol and ginger extract. The formulation disclosed has a skin irritation reducing action comprising bisabolol and a composition or compound chosen from the group consisting of a) substance mixtures obtainable from an extraction of ginger, b) substance mixtures obtainable from a separation of a ginger extract which comprises a compound which is chosen from the group consisting of gingerols, shogaols, gingerdiols, dehydrogingerdinoes, paradols and derivatives thereof and c) compounds obtainable from a separation of a ginger extract which are chosen from the group consisting of gingerols, shogaols, gingerdiols, dehydrogingerdiones, paradols and derivatives thereof and mixtures thereof, wherein in particular content of bisabolol and of the said compositions or compound in the formulation is adjusted such that the skin irritation-reducing action is these contents is increased synergistically.

In addition to the above, a U.S. Pat. No. 7,744,931 of Newmark et al. discloses a method for treating oral cancers with herbal compositions. The method comprises administering a composition comprising therapeutically effective amounts of supercritical extracts of rosemary, turmeric, oregano and ginger and therapeutically effective amounts of hydroalcoholic extracts of holy basil, ginger, turmeric, *Scutellaria baicalensis*, rosemary, green tea, huzhang, Chinese goldthread, and barberry. The inventive subject matter further relates to methods for modulating gene expression of genes selected from the group consisting of interleukin-1α, interluekin-1β, heme oxygennase 1, aldo-keto reductase family 1, member C2, colony stimulating factor 3, leukemia inhibitory factor, heat shock 70 kDa protein, and combinations thereof, by administration of an effective amount of said compositions.

Finally, a U.S. Pat. No. 7,777,073 of Gupta discloses a topical delivery system for antiaging and skin whitening agents. As disclosed, a certain hydroxyaryl alkanols, alkyl amines, alkyl amino alkanols ("Hydroxyaryl compounds") of formula (1). A method of topical application of said hydroxyaryl compounds is also disclosed. The treatment of certain enzyme dysfunctions that cause skin or hair conditions such as darkened skin including age spots, dark circles around the eyes, and discoloration of skin from stretch marks; skin conditions related to acne including excess facial oil and facial pore size; premature hair aging including hair loss and graying; inflammation including intra-cellular and extra-cellular inflammation; skin aging including wrinkles and the fine lines; loss of collagen including thinning skin and loss of skin pliability; malfunction of tyrosinase group of enzymes; and malfunction of matrix metalloprotease group of enzymes with said hydroxyaryl compounds is also disclosed.

Each of the above references is incorporated herein in their entirety by reference.

Notwithstanding the above it is presently believed that there is a need and a potential commercial market for improved compositions and methods for the treatment and management of pain in human patients. There should be a commercial market because such compositions and methods have been shown to produce greater than expected results and a reduction of pain in over 72% of respondents who responded completely too somewhat less pain after using a topical pain relief cream for one to two weeks. Over 90% of the respondents reported that completely to somewhat agreed that the topical cream was easy to use while 60% said that it was effective for pain management and 96% agreed completely that the odor-free benefit was very important. Further, when probed on continued interest in the product 72% agreed that they were interested in using the product beyond the trial period and almost 60% felt that the product not only exceeded their expectations, but that they were extremely satisfied with the product as well. A survey also indicated customer feedback on the ingredients, formulation and field of product.

Overall, respondents like this natural pain relief cream; 70% somewhat to completely agreed that the natural formulation was important to them and 80% agreed with the statement "I like the way the product feels on my skin". 100% of respondents agreed that it was important that the product was non-greasy and 96% agreed that it was important that the cream had no side effects. Of the entire group, 72% were interested in the continued use of the product. In addition, a majority of the users reported pain reduction and 20% indicated a level of 5-6 i.e. moderate to severe pain down from 50% at the start of the trial.

BRIEF SUMMARY OF THE INVENTION

In essence, the present invention contemplates an herbal organic composition for the management of pain. The herbal/organic composition comprises and/or consists of turmeric extract, *Boswellia* extract, ginger extract, holy basil extract, rosemary extract, white willow bark extract, alpha lipoic acid and trolamine salicylate and a topically acceptable carrier.

In a preferred embodiment of the invention the herbal/organic composition consists of about the pharmaceutically acceptable carrier selected from the group consisting of water, glycerol stearate, octinoxate, alphotocapherol (vitamin E), diazolidimylurea, Coco Caprylate/Caprate and Sterearyl Stearate.

A further embodiment a composition for the management of pain according to claim 6 in which the turmeric extract has been normalized to comprise about 95% curcuminoids, the *Boswellia* extract has been normalized to comprise about 65% boswellic acid, the ginger extract has been normalized to comprise about 5% gingerols, the holy basil extract has been normalized to comprise about 2% ursolic acid, the rosemary extract (*Rosmarinus officialis*) (leaf) is standardized to 6% Carmosic acid, and the willow bark extract (bark) is standardized to 15% total salicin.

DESCRIPTION OF THE PREFERRED EMBODIMENTS OF THE INVENTION

The present invention relates to compositions and methods for the treatment and management of pain in a subject. Although herbal extracts have been used for the treatment and management of pain, new and more effective formulations for the treatment and management of pain are provided herein.

As used herein, the term "pain" refers to acute and chronic pain, including pain caused by trauma or inflammation such as back pain, toothache, headache, and menstrual cramps, sore throat, fever, and rheumatic pain such as joint pain, gouty arthritis, ankylosing spondylitis, rheumatoid arthritis, and pain associated with systemic connective tissue disorders, cancer, neuropathy and referred pain.

As used herein, the term "treatment and management of pain" refers to pharmacologic measures that lead to the amelioration of the symptom. Such treatment or management of pain is sufficient to eliminate or significantly reduce pain or the effects of pain. More specifically, such pharmacological measures include the administration of the mixture described herein to a subject either topically or orally to ameliorate or relieve pain.

As used herein, "therapeutically effective amount" refers to the amount (dose) of a composition sufficient for the treatment or management of pain in a subject. Determination of a therapeutically effective amount or dose is determined by one of skill in the art according to the desired effect, e.g., degree to which pain is treated or managed.

As used herein, the term "subject" refers to an animal, in particular, a mammal, e.g., a human.

The components of the compositions of the present invention include, but are not limited to, white willow bark extract, rosemary extract, ginger extract, turmeric extract, *Boswellia* extract, holy basil extract and alpha lipoic acid. These components can be, for example, normalized to a particular active compound or compound present within the extract.

Alpha Lipoic Acid

Alpha Lipoic Acid is also called lipoic acid, thioctic acid, or ALA. It is a fatty acid found naturally inside every cell in the body. Alpha lipoic acid converts glucose (blood sugar) into energy.

Alpha lipoic acid is also an antioxidant, a substance that neutralizes potentially harmful chemicals called free radicals. What makes alpha lipoic acid unique is that it functions in water and fat, unlike the more common antioxidants vitamins C and B, and it appears to be able to recycle antioxidants such as vitamin C and glutathione after they have been used up. Glutathione is an important antioxidant that helps the body eliminate potentially harmful substances. Alpha lipoic acid increases the formation of glutathione.

Alpha lipoic acid is made by the body and can be found in very small amounts in foods such as spinach, broccoli, peas, Brewer's yeast, brussel sprouts, rice bran, and organ meats.

Alpha lipoic acid supplements are available in capsule form at health food stores, some drugstores, and online. For maximum absorption, the supplements should be taken on an empty stomach.

Alpha lipoic acid may help treating peripheral neuropathy that can be caused by injury, nutritional deficiencies, chemotherapy or by conditions such as diabetes, Lyme disease, alcoholism, shingles, thyroid disease, and kidney failure. Alpha lipoic acid is thought to work as an antioxidant in both water and fatty tissue, enabling it to enter all parts of the nerve cell and protect it from damage. The dose that is best tolerated while still providing benefit is 600 mg, once daily.

Alpha lipoic acid can cross the blood-brain barrier, and pass easily into the brain. It is thought to protect brain and nerve tissue by preventing free radical damage.

As an antioxidant, alpha lipoic acid can neutralize free radicals that can damage cells, and helps age-related conditions and chronic illnesses. Alpha lipoic acid has also been suggested for use to treat or manage cataracts, glaucoma, multiple sclerosis, burning mouth syndrome, Alzheimer's disease and stroke.

The extracts and alpha lipoic acid can be used as ingredients, for example, in compositions that can be used to treat or ameliorate pain or conditions associated with pain. Two, three, four, five, six or more of the extracts can be used as ingredients in such compositions, with or without alpha lipoic acid. Such compositions can also comprise additional extracts as determinable by one of skill in the art.

Boswellia Extract

Boswellia, known also as *Boswellia serrata*, is a branching tree that is native to India. It grows in dry, hilly regions of the country and produces a resin that can be extracted and purified for medicinal preparations.

Boswellia extract is best known among herbalists as a treatment for arthritis. One of its primary active ingredients, boswellic acid, is an anti-inflammatory that can be used in ointments to ease joint pain. *Boswellia* extract can also be taken internally as an anti-inflammatory agent, much like NSAIDs (non-steroidal anti-inflammatory agents), such as ibuprofen, which is commonly used to treat pain. However, unlike NSAIDs, *Boswellia* extract can be used for significant periods of time without causing stomach upset.

Boswellia extract is available in capsules, with extracts standardized for boswellic acids. The recommended dosage to treat arthritis is the amount that contains 150 mg of boswellic acids, taken three times per day.

Ginger Extract

Ginger is a tuber that is consumed whole as a delicacy, medicine or used for cooking or tea. It is the underground stem of the ginger plant, *Zingiber officinale*. The medicinal form of ginger historically was called "Jamaica ginger"; it was classified as a stimulant and carminative, and used frequently for dyspepsia and colic. It was also frequently employed to disguise the taste of medicines. Ginger is on the FDA's "generally recognized as safe" list, though it does interact with some medications, including warfarin. Ginger is contraindicated in people suffering from gallstones as the herb promotes the release of bile from the gallbladder. Ginger also decreases joint pain from arthritis, though studies on this have been inconsistent, and may have blood thinning and cholesterol lowering properties that may make it useful for treating heart disease. Ginger and its extract have been used against diarrhea and nausea caused by seasickness, morning sickness and chemotherapy, though ginger was not found superior over a placebo for post-operative nausea.

Ginerrol, or sometimes [6]-gingerol, is the active constituent of fresh ginger. Chemically, gingerol is a relative of capsaicin, the compound that gives chile peppers their spiciness. It is normally found as a pungent yellow oil, but also can form a low-melting crystalline solid. Cooking ginger transforms gingerol into zingerone, which is less pungent and has a spicy-sweet aroma. Gingerol may reduce nausea caused by motion sickness or pregnancy and may also relieve migraine. In the West, powdered dried ginger root is made into capsules and sold in pharmacies for medicinal use.

Holy Basil Extract

Holy Basil (*Ocimum tenujfiorum* or *Ocimum sanctum*) has been shown to possess powerful adaptogenic properties and has been used to enhance the body's ability to respond to stress and minimize the negative effects of stress on the body. Animal studies have demonstrated that holy basil can support carbohydrate metabolism and, as a result, healthy blood glucose levels. Holy basil is revered as a sacred plant in Ayurveda, the traditional therapeutic system of India.

Studies have shown holy basil leaves have properties similar to the anti-TB drugs like Streptomycin and Isoniazide. Essential oil of holy basil has been used as a potent antimalarial drug. It also has mosquito repellent properties. Research has also shown that holy basil acts as an antioxidant and decreases stress hormones. It is a powerful anti-inflammatory similar to aspirin and ibuprofen, but unlike aspirin and ibuprofen it is not irritating to the stomach and in fact, it has properties that help to prevent ulcers caused by these drugs.

As an herbal dietary supplement, the extract is standardized to 2% Ursolic Acid and is taken 1-2 times daily, preferably with meals.

Rosemary Extract

Rosemary (*Rosmarinus officinalis*) and its extract are well-known for food seasoning and cosmetics. Additionally, rosemary extract has been used to treat a wide range of ailments. Orally, rosemary is used for upset stomach, digestive disorders and headaches, inducing abortion, increasing menstrual flow, gout, liver and gallbladder complaints, and for cardiovascular conditions such a high blood pressure. Topically, rosemary is used for preventing baldness, alopecia areata, circulatory disturbances, toothache, eczema, joint or musculoskeletal pain such as myalgia, sciatica and intercostal neuralgia, balneotherapy, wound healing, and as an insect repellent. Rosemary extract also allegedly helps prevent cancer and age-related skin damage, boosts the functioning of the liver and acts as a mild diuretic to help reduce swelling.

The applicable part of rosemary is the leaf. The active constituent of rosemary leaves is the essential oil. Dried leaves contain from 1-2.5% of the essential oil. The oil consists primarily of cineole, bomeol, bomyl acetate, camphor, camphene, pinenes, and a-terpineol. Other compounds are diterpenes (picrosalvin, carnosolic acid, rosinariquinone), poliphenols: caffeic acid and rosmarinic acid, flavonoids (apigenin, diosmetin, diosmin, genkwanin, hispidulin, sinensetin, luteolin), and triterpenes (ursolic acid). Diterpenoids have been shown to be effective to protect biological systems against oxidative stresses.

Trolamine Salicylate

Trolamine salicylate is an organic compound which is a salt formed between triethanolamine and salicylic acid according to Wikipedia, the Free Encyclopedia.

The organic compound is frequently used as an ingredient in sunscreen, creams and cosmetics. Triethanolaminem neutralizes the acidity of the salicylic acid. Benefits of this topical analgesic is that it has no odor in contrast to topical analgesics such as menthol.

As stated by Wikipedia, one study reported that trolamine salicylate does penetrate into, and persists within underlying muscle tissue. The study indicated that individuals using the trolamine salicylate product reported slower onset of soreness, reduced levels of soreness and reduced duration of soreness as compared to those using a placebo.

Turmeric Extract

Turmeric extract is a bright yellow/orange polyphenol having the form of a dry powder that is fat-soluble. The concentrate has neither flavor nor aroma. It colors food readily if there is oil present. The medicinal properties and health benefits of turmeric extract are attributed partly to its strong anti-oxidant and anti-inflammatory characteristics. Turmeric extract is derived from the root of the turmeric plant first by drying and then by separation using a solvent. There are 18 times more curcuminoids in the concentrate than in the natural spice, which is simply a powdered form of the dried root. The concentrate is also known as Curcumin Turmeric extract has attracted the attention of researchers in the fields of Alzheimer's disease, memory deficits, arthritis, cancer (including breast cancer), and diabetes. The plant has the botanical name of "Curcuma Longa Linn," and is a member of the Zingiberaceae or ginger family. Its source is India but it is now cultivated in China and elsewhere. It grows to one meter in height and has long oblong leaves. Beneath the foliage, in the ground, are the rhizomes from which the food coloring is derived. The effect or benefits of turmeric extract are as an anti oxidant, as anti-inflammatory, as anti-dyspepsia, to break up Alzheixner's ainyloid-beta oligomers and aggregates, for its anti-platelet effects, and to cause apoptosis (death) of various malignant cell types including skin, colon, forestomach, duodenum and ovary.

Turmeric extract can be obtained with a normalized curcuminoid content of 95% plus. Customary usage of turmeric extract is about 1-2.5 g per day.

White Willow Bark Extract

The white willow bark extract can be used as an analgesic and antipyretic for the treatment of pain and inflammation. An active constituent of the extract is salicin, an anti-inflammatory agent that is produced from all willow barks. Salicin is an alcoholic β-glycoside that contains glucose. Salicin is closely related in chemical makeup to aspirin and has a similar action in the human body. When consumed, it is metabolized to salicylic acid.

Although active agents present in extracts can be purified and used, complications and impurities associated with synthesis and/or purification of the purified active agents make purified active agents undesirable. The use of extracts as described herein, allows for the safe administration of naturally occurring compositions. In addition, extracts contain a combination of other compounds that can also have therapeutic or ameliorative benefits.

Obtaining extracts from natural sources leads to variability of composition from batch to batch. As such, the extracts described herein can be normalized such that the extract contains a certain percentage of a particular compound, e.g., an active agent. *Boswellia* extract, for example, can be normalized to comprise about 50% to about 95% boswellic acids, about 60% to about 80% boswellic acids, about 65% boswellic acids, about 70% boswellic acids, or any normalized percentage suitable for use in the compositions described herein. Ginger extract, for example, can be normalized to comprise about 0.5% to about 10% gingerols, about 0.25% to about 8% gingerols, about 1% gingerols, about 2% gingerols, or any normalized percentage suitable for use in the compositions described herein.

Holy basil extract, for example, can be normalized to comprise about 0.5% to about 20% ursolic acid, about 1% to about 10% ursolic acid, about 2% ursolic acid, about 1% ursolic acid, or any normalized percentage suitable for use in the compositions described herein. Rosemary extract, for example, can be normalized to comprise about 5% to about 40% diterpenes, about 10% to about 30% diterpenes, about 20% diterpenes, about 25% diterpenes, or any normalized percentage suitable for use in the compositions described herein. Willow extract, for example, can be normalized to comprise about 2% to about 35% salicin, about 5% to about 20% salicin, about 15% salicin, about 20% salicin, or any normalized percentage suitable for use in the compositions described herein.

Compositions described herein contain a therapeutically effective amount of six extracts and lipoic acid. One of skill in the art would be able to determine a therapeutically effective dose. A normalized extract, for example, can comprise about 0.01%, about 0.5%, 1.0%, 2.5%, 5% or greater, of the therapeutic compositions described herein.

Compositions described herein can comprise, for example, ingredients that aid in the delivery and/or preservation of the active agents. Compositions can comprise, for example, excipients, pharmaceutically-acceptable carriers, preservatives and/or delivery agents/vehicles. An excipient is an inactive substance used as a carrier for the active ingredients of a medication. In some cases, an active substance may not be easily administered and absorbed by the human body. In such cases the substance in question can be mixed with an excipient.

Excipients can also be used to bulk up formulations that contain very potent active ingredients, to allow for convenient and accurate dosage. In addition to their use in the single dosage quantity, excipients can be used in the manufacturing process to aid in the handling of the active substance concerned. Depending on the route of administration, and form of medication, different excipients may be used, as determined by one of skill in the art.

Pharmaceutically-acceptable carriers can include, for example, creams and compositions that allow for the diffusion or active transport of active agents across the skin for use in, for example, compositions that are to be administered topically. Alternatively, carriers can be suited to oral administration, for example, by allowing diffusion of active agents from capsules or tablets. Such carriers are known to those of skill in the art and can be selected according to the mode of administration.

The compositions of the present invention can be administered in any pharmaceutically-acceptable manner. Compositions for topical and oral administration are described, however the compositions described herein can also be administered, for example, rectally, intravenously or subcutaneously using, for example, an implantable device.

EXAMPLES

Example 1

Background:

A clinical comparison study was conducted to test the efficacy of a topical herbal medication for inflammatory and chronic pain relief in adults over the age of 18. The participants tested the products over a 7-day period and then evaluated them for the efficacy of the herbal medication through pre and post study questionnaires. Conclusions were drawn based on the responses of the participants regarding pain relief at the end of the 7-day period.

Subject Selection:

Subjects included adults (age 18 years or older) able to provide written informed consent for study participation and able to fully participate in this study. The study did not intend to examine chronic or inflammatory joint pain reduction in any specific race or ethnicity or gender, therefore subjects included any race/ethnicity. Subjects who have inflammatory joint pain due to Rheumatoid Arthritis, and/or other inflammatory conditions, chronic muscle pain and spasms, and neuropathic joint pain due to diabetes were considered for the study. The study did not include any participants who were pregnant, had been diagnosed of psychiatric disorders, brain disorders or showed an inability to communicate. Subjects with medical condition that contradicted the use of herbal medications were not included in the study. Questionnaires to evaluate pain were given to the subjects prior to the start, and the end of the study to evaluate pain relief.

The subjects were recruited from all races/ethnicities to the extent possible. Participants were recruited from across the Washington, DC, Maryland and Virginia area, and were afflicted by chronic and inflammatory joint pain, chronic muscle pains and spasms. The study made every attempt to assure adequate representation of each minority/ethnic group. A total of 50 subjects were recruited for the study, with 25 participants being used in a control group, and 25 in a treatment group.

Procedures:

The subjects were divided into treatment and control groups by random assignment, and given a consent form and a 7-day supply of the topical product. Subjects were instructed to apply the topical cream 3-4 times daily (at the site of pain) for the 7-day period. Instructions on the use of the medications were provided at the start of the study, and the participants agreed not to let anyone else use the product. They assessed their pain through questionnaires in English on two occasions; at the start of the study, and at the end of the study. The questionnaires required about 10-15 minutes to complete while the time for using the medications was minimal, about the time required to apply an ointment. No participant was paid, or received any sort of compensation, for agreeing to participate in this study.

Consent Forms and Information

Subjects were included as part of the study only after they read and understood the informed consent form, which was available in English only. The subjects were informed about the objective of the study—to evaluate the efficacy of a newly formulated herbal medication to relieve chronic and inflammatory joint pain. Instructions to use the medications were provided separately to the group and subjects were informed of the risks involved in improper use of the medication, and given written instructions on using the products. The informed consent forms were required to be read and signed personally by the subjects before being included in the study.

Survey

A pre and post study survey was created to gather participant feedback on the all natural pain-relief cream created to treat chronic and inflammatory joint pain. The pre study questionnaire probed the level of pain each participant experienced through a variety of questions designed to capture as much information as possible on the type of pain, location, and severity. The post study questionnaire asked participants to rate their pain experience after having used the topical pain relief cream, and was designed to capture information on type of pain relief experienced, and perceptions and intent towards the topical pain cream after having used it for the 7-day period.

Results—Treatment Group

To create a benchmark for the effectiveness of the cream, participants were asked to rate their current type and level of pain on day one of the study. (The control group reflected the treatment group to the type and level of pain, and there was no relevant or statistical change to the type or frequency of pain for the control group over the 7-day period, and these results reflect responses from the 25 participants in the treatment group.)

Three different types of pain were assessed in the study: chronic, muscular or nerve and of these three types, over 68% percent of respondents described their pain as muscular.

Muscular pain included acute muscle aches from a sporting injury, pain from conditions such as fibromyalgia or cancer treatments, and involved ligaments, tendons, bones and organs. Chronic or acute pain and inflammation, which included side-effects like burning or swelling, accounted for over 48% of respondents, while 20% reported their pain as nerve pain - burning, throbbing or stinging.

Participants were also asked to rate their level of pain at the start of the study survey. On a scale of 1-10 (with 1 being no pain, and 10 being unbearable pain), over half rated their pain level at a 5-6; moderate to severe pain that was discomforting and distressing. None of the respondents indicated any pain, or unbearable pain, and mild to moderate pain was the next highest reporting group at 24%.

After using the product for seven days, respondents were again asked to assess their level of pain and inflammation, as well as their opinions on the efficacy and formulation of the natural pain relief cream. By day seven, when asked, "I feel like I have less pain", over 72% of respondents completely too somewhat agreed that their level of pain was reduced after using the topical pain relief cream. In addition, nearly 60% of users reported a reduction in inflammation. Respondents were also asked a series of questions about the mechanics of using the cream. Over 90% of respondents completely to somewhat agreed that the topical cream was easy to use. Nearly 60% felt the cream was effective for pain management and 96% agreed completely that the odor-free benefit was very important. When probed on continued interest in the product, 72% agreed they were interested in using the product beyond the trial period, and almost 60% felt the product not only exceeded their expectations, but that they were extremely satisfied with the product, as well.

The survey also captured consumer feedback on the ingredients, formulation, and feel of the product. Overall, respondents liked this natural pain relief cream. 72% somewhat to completely agreed that the natural formulation was important to them, and 80% agreed with the statement, "I like the way the product feels on my skin". 100% of respondents agreed that it was important the product was non-greasy, and 96% agreed that was important the cream had no side-effects. Of the entire group, 72% were interested in continued use of this product. When asked again to assess their level of pain on a scale of 1-10 (1 being zero pain and 10 being unbearable pain), the majority of uses reported pain at a level 2-3, little to mild pain. Even more important, only 20% indicating a level 5-6, moderate to severe pain—down from 50% at the start of the trial.

Conclusions

While at the start of the study, over 50% of participants rated their pain as moderate to severe, by day seven, 72% of users reported a reduction in their level of pain, and 56% reduction in inflammation. At the end of the survey, only 20% of participants rated their pain as moderate to severe, and 48% indicated they have very little to no pain. Importantly, 92% of users felt the product was easy to use, 80% of participants liked the way the product felt on the skin, and 100% of users felt the non-greasy texture of the cream was important.

Overall, participants were interested in the product, liked the formulation and ease of use, and felt (and noticed) a reduction in their level of pain. The all-natural ingredient profile, the fact that the product had no odor, and didn't leave the skin feeling greasy were all extremely important benefits to the users, indicating that for pain sufferers, aesthetics are just as important as esthetics when it comes to treating their pain. According to the participants' comments, they don't want a perfunctory, mundane treatment they want a solution that will also appeal to their senses and fit in with their lifestyle. The other benefit that was extremely important to participants, the fact that the cream had no side-effects—further supports the idea that a topical pain relief cream must answer more than just the question of pain, it should take into account overall health, as well.

Perhaps due to unsatisfactory experiences with other topical pain relief creams, participants in this study were surprised to find the product exceeded their expectations.

Accordingly, interest in continued use of the product was high, as was the inclination to recommend the product to others. Taking into account the fact that, overall, users reported a reduction in their the level of pain, as well as the user benefits and high continued-interest in the product, the data suggests that the topical pain cream of the present invention meets a need in the art that is not currently being met.

Example 2

Background and Purpose

Patients with muscle and joint dysfunction often experience waxing and waning episodes of inflammation. The purpose of this study was to evaluate the efficacy of the topical herbal formulation of the present invention in assisting patients with management of these episodes.

Study Description

A total of 30 subjects with a variety of musculoskeletal diagnoses were chosen for the study. The diagnoses included: cervical strain, lumbar strain, knee sprain, shoulder sprain, knee osteoarthritis, hand osteoarthritis and tendinitis of the knee, elbow and shoulder. All subjects received an initial week of therapy without the use of the topical herbal formulation. Pain and irritation was evaluated at the start of treatment and at the end of the initial week using the visual analog scale (VAS). Following the initial week of therapy, no changes were made in the plan of care except for the addition of the topical herbal formulation, which was used during each treatment for a period of two weeks. Each subject was also given a tube for use at home. Subjects were instructed to apply liberally 2-3 times per day for a period of two weeks. Return demonstration was required by each subject to ensure proper application. Pain assessments were performed weekly using the VAS. The results are shown in Table I below:

TABLE 1

| Subject | Diagnosis | Pain at Trial Start | Pain at Trial End | Percentage Change |
|---|---|---|---|---|
| 1 | Tennis elbow | 7 | 3 | 57% |
| 2 | MCL sprain | 5 | 2 | 60% |
| 3 | Lumbar strain | 6 | 4 | 33% |
| 4 | Shoulder strain | 4 | 0 | 100% |
| 5 | Cervical strain | 6 | 2 | 67% |
| 6 | Cervical strain | 6 | 3 | 50% |
| 7 | Knee osteoarthritis | 7 | 1 | 86% |
| 8 | Wrist osteoarthritis | 8 | 4 | 50% |
| 9 | Lumbar strain | 7 | 7 | No change |
| 10 | Knee osteoarthritis | 8 | Returned cream | — |
| 11 | Cervical strain | 5 | 2 | 60% |
| 12 | Foot pain | 4 | 4 | No change |
| 13 | Shoulder strain | 6 | 3 | 50% |
| 14 | Patella tendonitis | 4 | 1 | 75% |
| 15 | Achilles tendonitis | 5 | 5 | No change |
| 16 | Biceps tendonitis | 8 | 7 | 13% |
| 17 | Lumbar strain | 8 | 5 | 38% |
| 18 | Cervical strain | 7 | 2 | 71% |
| 19 | Hand osteoarthritis | 5 | 4 | 20% |
| 20 | ACL sprain | 6 | 2 | 67% |
| 21 | Medial epicondylitis | 7 | 6 | 14% |
| 22 | Tennis elbow | 5 | 2 | 60% |
| 23 | Biceps tendonitis | 4 | 1 | 75% |
| 24 | Knee osteoarthritis | 7 | 4 | 43% |
| 25 | Wrist osteoarthritis | 7 | 3 | 57% |
| 26 | Lumbar strain | 6 | 5 | 17% |
| 27 | Patella tendonitis | 4 | 1 | 75% |
| 28 | Rotator cuff tendonitis | 6 | 2 | 67% |
| 29 | Cervical strain | 9 | 6 | 33% |
| 30 | MCL sprain | 7 | 5 | 29% |

Results

A total of 60% of the patients had a 50% or more reduction in pain during the 2-week 5 trial, while 90% of the patients had some reduction in pain during the 2-week trial. Only one patient returned the cream and refused to continue with the study and only three patients had no change.

Conclusion

The data suggests that the herbal formulation of the present invention is useful for reducing musculoskeletal pain and inflammation.

While the invention has been described in connection with its preferred embodiment it should be recognized that changes and modifications may be made therein without departing from the scope of the appended claims.

What is claimed is:

1. A method for treating pain in a human in need thereof consisting essentially of:

topically administering to the skin of said human in need thereof therapeutically effective amounts of turmeric extract, Boswellia extract, ginger extract, holy basil extract, rosemary extract, white willow extract, alpha lipoic acid and trolamine salicylate for three or four times a day at the site of pain of the human in need thereof.

2. The method of claim 1, wherein the therapeutically effective amounts are 0.01 wgt % turmeric extract, 0.01 wgt % Boswellia extract, 0.01 wgt % ginger extract, 0.01 wgt % holy basil extract, 0.01 wgt % rosemary extract, 0.01 wgt % white willow extract, 0.01 wgt % alpha lipoic acid and 10.0 wgt % trolamine salicylate.

3. The method of claim 1, wherein the topical administration is in cream form.

4. The method of claim 3, wherein the cream consists essentially of water, glycerol stearate, octinoxate, alphotocapherol (vitamin E), diazolidimylurea, Coco Caprylate/Caprate, Sterearyl Stearate, or mixtures thereof.

5. The method of claim 1, which is repeated for seven to 14 days.

\* \* \* \* \*